United States Patent [19]

Yajima et al.

[11] 4,128,565

[45] Dec. 5, 1978

[54] PROCESS FOR PREPARING METHYLTIN CHLORIDES

[75] Inventors: Kunihiko Yajima, Yokohama; Shuji Sayama, Fuchu, both of Japan

[73] Assignee: Sankyo Organic Chemicals Company Limited, Kawasaki, Japan

[21] Appl. No.: 725,519

[22] Filed: Sep. 22, 1976

[30] Foreign Application Priority Data

Sep. 29, 1975 [JP] Japan .................. 50-117560

[51] Int. Cl.$^2$ ................................ C07F 7/22
[52] U.S. Cl. ................................ 260/429.7
[58] Field of Search ...................... 260/429.7

[56] References Cited

U.S. PATENT DOCUMENTS

| | | | |
|---|---|---|---|
| 3,387,011 | 6/1968 | Coates et al. | 260/429.7 |
| 3,415,857 | 12/1968 | Hoye | 260/429.7 |
| 3,475,473 | 10/1969 | Tahara et al. | 260/429.7 |
| 3,519,665 | 7/1970 | Molt et al. | 260/429.7 |
| 3,547,965 | 12/1970 | Takubo et al. | 260/429.7 |

OTHER PUBLICATIONS

Smith et al., J. A. C. S., 75, pp. 4103–4106, (1953).
Sisido et al., J. Arganometal, Chem. 9, pp. 109–115, (1967).
Oakes et al., J. Arganometal, Chem. 3, pp. 472–477, (1965).

*Primary Examiner*—Helen M. S. Sneed
*Attorney, Agent, or Firm*—Flynn & Frishauf

[57] ABSTRACT

Improved process for preparing methyltin chlorides through direct reaction of methyl chloride with metallic tin wherein the reaction is effected in a high-boiling hydrocarbon solvent in the presence of a glycol and iodine or an iodine compound as a reaction accelerator.

12 Claims, No Drawings

PROCESS FOR PREPARING METHYLTIN CHLORIDES

This invention relates to an improvement in preparation of methyltin chlorides.

More particularly, it is concerned with an improved process for preparing methyltin chlorides through direct reaction of methyl chloride with metallic tin, characterized in that the reaction is effected in a high-boiling hydrocarbon solvent in the presence of a combination of a glycol and iodine or an iodine compound as a reaction accelerator.

Methyltin chloride compounds have recently been developed for use as a stabilizer for polymer compounds, particularly, a stabilizer for a vinyl chloride resin, and for use as a glass coating agent, and, accordingly, its demand has increased. For this reason, excellent processes for preparing methyltin chloride which is a starting material for the synthesis of such compounds have been strongly desired.

Various processes for preparing methyltin chloride have been proposed heretofore, and these processes are roughly classified into Grignard method and Direct method.

According to the Grignard method, a methylmagnesium halide is, in the first stage, synthesized by reacting a methyl halide with magnesium in an ethereal solvent using an initiating agent such as iodine. Then, the resulting halide is reacted with tin tetrachloride to convert the latter into tetramethyltin. After isolation, this product is further subjected to redistribution reaction with tin tetrachloride to obtain the desired trimethyltin chloride, dimethyltin dichloride or methyltin trichloride.

As stated above, the Grignard method necessarily uses expensive magnesium and a large amount of an ether and involves multiple and complicated steps. Therefore, this process contains a lot of disadvantageous factors.

As for the Direct method, it is reported that processes for preparing methyltin chloride directly from methyl chloride and tin of the starting compounds may employ various kinds of reaction accelerators as mentioned below.

For instance, there are mentioned a process employing three elements consisting of an iodine compound, an organic solvent such as n-butanol or tetrahydrofuran and a very small amount of magnesium [Japanese Patent Publication (JPP) No. 19116/63]; process employing an iodine compound and an organic phosphoric compound (JPP 3617/66); process employing an iodine compound and an organic nitrogen compound (JPP 6739/66); process employing an iodine compound and an inorganic nitrogen compound (JPP 2341/67); process employing one or two of iodine and an alkyl iodide (JPP 13738/66); etc.

All of these processes are carried out at a high pressure in an autoclave, and therefore these processes may only be employed with danger in industry. In addition, enlargement to the industrial scale cannot be practised.

On the other hand, there are known direct reaction processes carried out at atmospheric pressure which employ such reaction accelerators as a combination of an iodine compound and an organic sulfone (Japanese Provisional Patent Publication No. 109323/74) and a so-called onium salt, e.g., tetraalkylammonium iodide or tetraalkylphosphonium iodide (British Pat. No. 1,222,642).

Yet, the reaction accelerators used in the above processes are very expensive, and hence their losses caused by heat decomposition, etc., during the reactions are serious drawbacks of these processes.

We have conducted research for the purpose of finding a process for preparing methyltin chlorides in high yields comprising a direct reaction of methyl chloride and tin at atmospheric pressure which employs an economical reaction accelerator. As a result, we have found that methyl chloride and tin can be reacted in a high-boiling solvent (boiling point, 120°–400° C.) at 120°–300° C., using a small amount of a reaction accelerator consisting of a glycol and iodine or an iodine compound so as to consume most of the charged tin, whereby methyltin chlorides can be obtained in high yields. Further, it has been noted that a methyltin chloride product obtained by this reaction comprises a greater part of dimethyltin dichloride which is industrially most valuable, and less than 1% of trimethyltin chloride.

It is, accordingly, a primary object of this invention to provide an improvement in a process for preparing methyltin chlorides which is commercially advantageous.

The above and other objects and advantages of this invention will become clearer from the following detailed description.

According to this invention, there is provided an improved process for preparing a methyltin chloride through direct reaction of methyl chloride with metallic tin, characterized in that the reaction is effected in a high-boiling hydrocarbon having a boiling point of about 120° C. to 400° C. at a reaction temperature of 120° C. to 300° C. in the presence of a reaction accelerator comprising (A) at least one glycol having the formulae $$C_mH_{2m}(OH)_2$$

wherein m is an integer of 2–10, $$HO(C_2H_4O)_nC_2H_4OH$$

wherein n is an integer of 1–10, $$HO(C_3H_6O)_pC_3H_6OH$$

wherein p is an integer of 1–8 and $$HO(C_2H_4S)_qC_2H_4OH$$

wherein q is an integer of 1–3; and
(B) iodine or an iodine compound selected from an alkali metal iodide having the formula $$MI$$

wherein M is an alkali metal, an alkyltin iodide having the formula $$R_wSnI_{4-w}$$

wherein R is a straight or branched alkyl group having 1–18 carbon atoms and w is an integer of 1–3, an alkyl iodide having the formula $$RI$$

wherein R is a straight or branched alkyl group having 4–18 carbon atoms, a metal iodide having the formula $$XI_2$$

wherein X is an alkaline earth metal or a divalent metal, a metal iodide having the formula $$YI_3$$

wherein Y is a trivalent metal and a metal iodide having the formula $$ZI_4$$

wherein Z is a tetravalent metal.

Embodiments of the present process are more fully described hereinbelow.

Into a reaction vessel are charged a high-boiling hydrocarbon as a solvent, tin, and a small amount of a glycol and iodine or an iodine compound as an reaction accelerator. The resulting mixture is kept at 120°–300° C., and into this mixture is introduced with vigorous stirring gaseous methyl chloride. The reaction instantly begins and the introduction of gaseous methyl chloride is continued until the charged tin disappears. After the reaction is complete, the produced methyltin chlorides are isolated from the reaction mixture, for instance, through a conventional distillation, and purified through recrystallization, redistillation, etc. In this case, the yield of the methyltin chlorides ranges from 40 to 60% based on the tin charged.

Separately, tin is freshly added to the so obtained distillation residue containing the reaction accelerator, and the reaction is repeated by introducing gaseous methyl chloride. On and after this second procedure, the tin is converted to methyltin chlorides in a high yield.

There is no need of adding repeatedly the glycol of the reaction accelerator in the second procedure. Iodine or an iodine compound is slightly lost during the distillation, and therefore when a small amount of it is again added to the reaction mixture, the reaction can proceed without decrease of the reaction rate. Some portion of the high-boiling hydrocarbon solvent may remain in the residue after the distillation, or may be distilled. However, since this distilled solvent can be recycled to be used repeatedly, there is hardly any loss.

As stated above, the process of this invention is superior to the conventional processes, because the former is smoothly carried out and completed at atmospheric pressure for a short period of time using as a reaction accelerator a glycol which is economically and easily available, and further because repeated reactions can be completed. In other words, the present process is of great economical advantage.

Methyltin chlorides may be prepared by reacting methyl chloride and tin in a large amount of a glycol in the presence of iodine or an iodine compound with no use of such a high-boiling hydrocarbon solvent, but in this case the reaction rate and the yield of the methyltin chloride decrease, as compared with those of the processes of the present invention.

The present reaction is carried out at a reaction temperature of 120°–300° C. The reaction rate will prominently decrease when the reaction is carried out at a temperature of below 120° C., and decomposition by heat will take place when the reaction is carried out at a temperature of higher than 300° C. More preferably, the present reaction may be carried out at 150°–230° C., and at temperatures in this range the reaction rate greatly increases and the yield of methyltin chlorides increases.

Glycols which can be used as the reaction accelerator in the process of this invention are exemplified as follows:

Glycols having the general formula $$C_mH_{2m}(OH)_2$$

in which m represents an integer of 2–10, for instance, ethylene glycol, propylene glycol, trimethylene glycol, α-butylene glycol, β-butylene glycol, tetramethylene glycol, sym-dimethylethylene glycol, pentamethylene glycol, hexamethylene glycol, pinacol, 2,2-dimethylolbutane, ethohexadiol, etc.:

Derivatives obtained by reaction of ethylene glycol with ethylene oxide having the general formula $$HO(C_2H_4O)_nC_2H_4OH$$

in which n represents an integer of 1–10, for instance, diethylene glycol, triethylene glycol, tetraethylene glycol, etc.:

Derivatives obtained by reaction of propylene glycol with propylene oxide having the general formula $$HO(C_3H_6O)_pC_3H_6OH$$

in which p represents an integer of 1–8, for instance, dipropylene glycol, tripropylene glycol, tetrapropylene glycol, etc.:

Thioglycols having the general formula $$HO(C_2H_4S)_qC_2H_4OH$$

in which q represents an integer of 1–3, for instance, thiodiglycol, etc.

Among the above-listed glycols, the glycols having the general formula $$HO(C_2H_4O)_rC_2H_4OH$$

in which r represents an integer of 1–4 are preferably employed in this reaction.

The glycols may be used in an amount of 0.1–10 times as much as the amount of tin charged as the starting material. When the glycol is charged in an amount of less than 0.1 time as much as the amount of tin, the reaction rate decreases, and when more than 10 times, the yield of the methyltin chlorides decreases. Preferred is the amount of 0.2–2 times as much as that of the charged tin.

In this reaction, either iodine or an iodine compound is used as another reaction accelerator. Either can be similarly effective on the reaction.

An iodine compound which may be used in the present reaction is a generally known compound and may be: an alkali metal iodide having the general formula $$MI$$

in which M represents an alkali metal, and I represents an iodine atom, for instance, lithium iodide, sodium iodide, potassium iodide, etc.;

an alkyltin iodide having the general formula $$R_wSnI_{4-w}$$

in which R represents a straight or branched alkyl group having 1-18 carbon atoms, and w represents an integer of 1-3, for instance, trimethyltin iodide, dimethyltin diiodide, methyltin triiodide, dibutyltin diiodide, dioctyltin diiodide, dilauryltin diiodide, etc.;

an alkyl iodide having the general formula $$RI$$

in which R represents a straight or branched alkyl group having 4-18 carbon atoms, for instance, octyl iodide, lauryl iodide, etc.;

a metal iodide having the formula $$XI_2$$

wherein X is an alkaline earth metal or a divalent metal, for instance, magnesium iodide, calcium iodide, stannous iodide, cupric iodide, etc.;

a metal iodide having the formula $$YI_3$$

wherein Y is a trivalent metal, for instance, aluminum iodide, etc.; or a metal iodide having the formula $$ZI_4$$

wherein Z is a tetravalent metal, for instance, stannic iodide etc.

Iodine or the iodine compound may be used in an amount of 0.01–0.02 mole, preferably 0.05–0.1 mole, per one gram atom of the charged tin.

The high-boiling point hydrocarbon which is used as a solvent has a boiling point of about 120°–400° C. If the boiling point is lower than 120° C., the reaction hardly proceeds, and if higher than 400° C., no advantage can be accomplished. In view of separation of the produced methyltin chlorides from the solvent through distillation, a hydrocarbon having a boiling point of about 250°–400° C. is preferably employed.

The hydrocarbon which can be employed in the present reaction may be exemplified as follow:

Aromatic hydrocarbons, namely, benzene-type hydrocarbons such as ethylbenzene, xylene, cumene, n-butylbenzene, t-butylbenzene, p-cymene, pentamethylbenzene, hexamethylbenzene, 1,3,5-triethylbenzene, hexaethylbenzene, amylbenzene, diamylbenzene, triamylbenzene, tetraamylbenzene, octylbenzene, dioctylbenzene, dodecylbenzene, didodecylbenzene, diphenylmethane, triphenylmethane, tetraphenylmethane, diphenyl, p-t-phenyl, stilbene, etc.; and naphthalene-type hydrocarbons such as naphthalene or alkylnaphthalenes, preferably having 1-3 ($C_1$-$C_{12}$) alkyl groups, e.g., monomethylnaphthalene, dimethylnaphthalene, trimethylnaphthalene, monoethylnaphthalene, diethylnaphthalene, triethylnaphthalene, monopropylnaphthalene, dipropylnaphthalene, tripropylnaphthalene, monobutylnaphthalene, dibutylnaphthalene, tributylnaphthalene, monohexylnaphthalene, dihexylnaphthalene, trihexylnaphthalene, monooctylnaphthalene, dioctylnaphthalene, trioctylnaphthalene, monodecylnaphthalene, didecylnaphthalene, tridecylnaphthalene, monododecylnaphthalene, didodecylnaphthalene, tridodecylnaphthalene etc. and paraffinic hydrocarbons such as n-octane, n-nonane, n-decane, dodecane, tetradecane, hexadecane, octadecane, eicosane, etc.

The amount of the hydrocarbon solvent used is 1–20 times as much as that of the tin of the starting material. When the amount is less than the amount of the tin, the mechanical stirring can hardly work, and when more than 20 times, the reaction rate decreases. An amount of 3–6 times is preferred.

Tin which is used in this process may be added in any form of powder, foil, shavings and bead. The surface area preferably is large so that the reaction rate may increase.

The present process will be more fully illustrated by the following examples. However, they are not intended to limit the scope of this invention.

EXAMPLE 1

(a) Into a 500 ml, four-necked flask equipped with a stirrer, a condenser, a methyl chloride gas-inlet tube and a thermometer were charged 68.6 g (0.578 gram atom) of shavings of tin, 34.3 g of diethylene glycol, 3.8 g of iodine and 308.7 g of tripropylnaphthalene (b.p. about 340° C.). Gaseous methyl chloride was introduced into the flask through the gas-inlet tube while the reaction mixture was vigorously stirred, being heated to 150°–160° C. on an oil bath. After 12 hours, all of the charged tin disappeared upon completion of the reaction. The reaction mixture was distilled under reduced pressure of 40 mmHg with heating, until the temperature of the residual liquid reached 200° C. The amount of the distillate was 80.6 g.

According to a gaschromatographic measurement, all of the methyltin chlorides amounted to 81.3 g. These methyltin chlorides were composed of 22.3 percent by weight of methyltin trichloride, 76.8 percent by weight of dimethyltin dichloride and 0.9 percent by weight of trimethyltin chloride. In this instance, the conversion ratio of the charged tin was 62.9%.

(b) To the distillation residue obtained in the above procedure-(a) was added 68.6 g of tin. Gaseous methyl chloride was introduced at 150° C. for 15 hours in the same manner as in (a) above. After that, all of the charged tin disappeared. Subsequently, the distillation was carried out to yield 116.1 g of a distillate, in which all of the methyl chlorides amounted to 100.4 g. These methyltin chlorides were composed of 7.2 percent by weight of methyltin trichloride, 92.2 percent by weight of dimethyltin dichloride, 0.6 percent by weight of trimethyltin chloride. In this instance, the conversion ratio of the charged tin was 78.6%.

(c) To the distillation residue obtained in the above procedure-(b) were added 68.6 g of tin and 1.9 g of iodide, and the reaction was carried out in the same manner. The distillation was conducted to yield 139.7 g of a distillate, in which all of methyltin chlorides amounted to 114.3 g. These methyltin chlorides were composed of 6.2 percent by weight of methyltin trichloride, 93.4 percent by weight of dimethyltin dichloride and 0.4 percent by weight of trimethyltin chloride. In this instance, the convertion ratio of the charged tin was 89.0%.

(d) To the distillation residue obtained in (c) above, were added 68.6 g of tin and 0.5 g of iodine, and the reaction was carried out in the same manner. The distillation was conducted to yield 143.7 g of distillate, in which all of the methyltin chlorides amounted to 124.0 g. These methyltin chlorides were composed of 8.6 percent by weight of methyltin trichloride, 90.7 percent by weight of dimethyltin dichloride and 0.7 percent by weight of trimethyltin chloride. In this instance, the conversion ratio of the charged tin was 97.8%.

(e) To the distillation residue obtained in (d) above were added 68.6 g of tin and 1.9 g of iodine, and the reaction was carried out in the same manner. The distillation was conducted to yield 153.8 g of a distillate, in which all of the methyltin chlorides amounted to 108.5 g. These methyltin chlorides were composed of 8.9 percent by weight of methyltin trichloride, 90.3 percent by weight of dimethyltin dichloride and 0.8 percent by weight of trimethyltin chloride. In this instance, the conversion ratio of the charged tin was 84.8%.

EXAMPLE 2

The reaction described in Example 1 was repeated except for using 190° C. as the reaction temperature. The reaction period of time shortened to approximately one third of that employed when conducted at 150° C. In this example, the yield of methyltin chlorides of the first reaction was 53.1%, that of the second 67.6% and that of the third 70.6%.

EXAMPLE 3

The reaction described in Example 2 was repeated except that triethylene glycol and iodine were used as the reaction accelerators. The yield of methyltin chlorides of the first reaction was 46.0%, that the second 65.3% and that of the third 78.4%.

EXAMPLE 4

The reaction described in Example 1 was repeated except for changing the solvent to dodecylbenzene. The yield of methyltin chlorides of the first reaction was 53.2%, and that of the second reaction 77.2%.

EXAMPLE 5

The reaction described in Example 1 was repeated except for changing the solvent liquid paraffin. The yield of methyltin chlorides of the first reaction was 45.5%, and that of the second reaction 70.5%.

EXAMPLE 6

The reaction described in Example 1 was repeated except that ethylene glycol and iodine were used as the reaction accelerators. The yield of methyltin chlorides of the reaction was 35.4%.

EXAMPLE 7

Into a 300 ml reaction vessel were charged 34.3 g of tin, 1.9 g of iodine and 102.9 g of diethylene glycol, and subsequently gaseous methyl chloride was introduced thereinto at 150° C. After about 20 hours, the charged tin disappeared upon completion of the reaction. The distillation was conducted, and the yield of methyltin chlorides in the distillate amounted to 34.0%.

What is claimed is:

1. In a process for preparing a methyltin chloride through direct reaction of methyl chloride with metallic tin, the improvement wherein the reaction is effected in a high-boiling hydrocarbon having a boiling point of from about 120° C. to 400° C. at a reaction temperature of from 120° C. to 300° C. and substantially atmospheric pressure in the presence of a reaction accelerator consisting essentially of (A) at least one glycol having the formulae $C_mH_{2m}(OH)_2$ wherein m is an integer of from 2 to 10, $HO(C_2H_4O)_nC_2H_4OH$ wherein n is an integer of from 1 to 10, $HO(C_3H_6O)_pC_3H_6OH$ wherein p is an integer of from 1 to 8 and $HO(C_2H_4S)_qC_2H_4OH$ wherein q is an integer of from 1 to 3; and
(B) iodine or an iodine compound having the formula

MI wherein M is an alkali metal.

2. A process according to claim 1 wherein said glycol is a compound having the formula $HO(C_2H_4O)_rC_2H_4OH$ wherein r is an integer of from 1 to 4.

3. A process according to claim 1 wherein said iodine compound is lithium iodide, sodium iodide or potassium iodide.

4. A process according to claim 1 wherein said hydrocarbon is an aromatic hydrocarbon having a boiling point of from about 120° C. to 400° C.

5. A process according to claim 1 wherein said hydrocarbon is an alkylnaphthalene having from 1 to 3 alkyl groups on the naphthalene ring, each alkyl group having from 1 to 12 carbon atoms.

6. A process according to claim 1 wherein said glycol is used in an amount of from 0.1 to 10 times as much as the amount of tin charged.

7. A process according to claim 1 wherein said iodine or iodine compound is used in an amount of from 0.01 to 0.20 mole per gram atom of the charged tin.

8. A process according to claim 1 wherein said hydrocarbon is used in an amount of from 1 to 20 times as much as the amount of tin charged.

9. A process according to claim 1 wherein said hydrocarbon is a hydrocarbon having a boiling point of from about 250° C. to 400° C., said reaction temperature is between 150° C. and 230° C., said glycol is a compound having the formula $HO(C_2H_4O)_rC_2H_4OH$ wherein r is an integer of from 1 to 4, and iodine, lithium iodide, sodium iodide or potassium iodide is used.

10. A process according to claim 1 which further comprises the steps of separation of a methyltin chloride from the reaction mixture and of addition of fresh metallic tin to the residue for reaction with methyl chloride left therein.

11. A process according to claim 1 wherein the methyltin chloride comprises a mixture of methyltin trichloride, dimethyltin dichloride and trimethyltin chloride.

12. A process according to claim 1 wherein the methyltin chloride is primarily dimethyltin dichloride.

* * * * *

UNITED STATES PATENT AND TRADEMARK OFFICE
CERTIFICATE OF CORRECTION

PATENT NO. : 4,128,565
DATED : December 5, 1978
INVENTOR(S) : KUNIHIKO YAJIMA et al It is certified that error appears in the above-identified patent and that said Letters Patent are hereby corrected as shown below:

Column 6, line 29: replace "80.6" with ---89.6---.

*Signed and Sealed this*

*Twenty-fifth* Day of *September 1979*

[SEAL]

Attest:

LUTRELLE F. PARKER

*Attesting Officer*    *Acting Commissioner of Patents and Trademarks*